United States Patent [19]
Yeung et al.

[11] Patent Number: 4,758,432
[45] Date of Patent: Jul. 19, 1988

[54] TOPICAL TREATMENT OF SKIN INFLAMMATORY DISORDERS

[75] Inventors: David Yeung, Stamford; Eugene Gans, Westport; Sergio Nacht, Weston, all of Conn.

[73] Assignee: Richardson-Vicks Inc., Wilton, Conn.

[21] Appl. No.: 660,899

[22] Filed: Oct. 15, 1984

[51] Int. Cl.$^4$ .............................................. A61K 35/78
[52] U.S. Cl. .................... 424/195.1; 514/763
[58] Field of Search ................. 424/195, 355; 514/763

[56] References Cited

U.S. PATENT DOCUMENTS 4,209,506 6/1980 Bouillon et al. ...................... 424/68
4,276,430 6/1981 Reller et al. ............................. 560/66
4,424,205 1/1984 Lahann et al. ......................... 424/72
4,431,673 2/1984 Goldner et al. ....................... 424/365

OTHER PUBLICATIONS

Chemical Abstracts 79: 103005n (Karryev et al), 1973.

*Primary Examiner*—Leonard Schenkman
*Attorney, Agent, or Firm*—Salvatore R. Conte; David K. Dabbiere; Douglas C. Mohl

[57] ABSTRACT

Method and pharmaceutical composition for topically treating skin inflammatory disorders by administering to the inflamed area a therapeutically effective amount of candelilla wax or a saturated hydrocarbon fraction from candelilla wax comprising a mixture of saturated straight chain $C_{29}$–$C_{33}$ hydrocarbons, predominantly $C_{31}$ hydrocarbon.

18 Claims, No Drawings

TOPICAL TREATMENT OF SKIN INFLAMMATORY DISORDERS

This invention relates to the discovery that candelilla wax and a certain fraction thereof affords an effective topical treatment for certain inflammatory skin conditions.

Candelilla wax is the wax obtained from the Candelilla plant and consists largely of hydrocarbons. It has now been found that candelilla wax and a certain fraction of the wax possess substantial vasoconstrictive activity suitable for topically treating inflammation in humans or animals. Said fraction consists essentially of a mixture of saturated straight chain $C_{29-33}$ hydrocarbons, as represented by the formula: $CH_3—(CH_2)_n—CH_3$, wherein n is an integer from 27 to 31, with the predominant hydrocarbon, about 80–85 percent by weight of the mixture, having a total of 31 carbons.

Both Candelilla wax itself and the aforementioned hydrocarbon fraction have been found to be therapeutically effective in treating inflammation of the skin, including acne. For purposes of this disclosure, the term "treating acne" is used to mean the temporary alleviation of the inflammation of the affected skin and other inflammatory signs and symptoms associated with acne.

In addition to treating acne, the superior vasoconstrictor activity of candelilla wax itself and the subject hydrocarbon fraction afford the usage thereof in an effective anti-inflammatory treatment for the following skin disorders: atopic dermatitis, atopic eczema, herpes simplex, shingles, poison ivy, poison oak, poison sumac and other skin allergic reactions, psoriasis, dandruff, and the like. As with acne, the term "anti-inflammatory treatment" or its equivalent is used to mean the temporary alleviation of the inflammation of the affected skin and other inflammatory signs and symptoms associated with the particular skin disorder.

Suitable pharmaceutical carriers for the topical administration of candelilla wax and the subject hydrocarbon fraction are non-polar pharmaceutical vehicles in conventional forms such as solutions, lotions, emulsions, ointments, gels, etc., in which the pharmaceutical carrier merely provides a physical form for the effective topical application of the active component to the skin. The therapeutic composition is prepared by simply mixing the desired therapeutically effective amount of the candelilla wax or the hydrocarbon fraction with the particular carrier according to conventional pharmaceutical compounding techniques.

By a "therapeutically effective amount" is meant an amount which is effective to alleviate the inflammation of the dermatological condition and yet cause substantially no undesirable side effects (at a reasonable benefit/risk ratio). In general, the candelilla wax and the subject hydrocarbon fraction are each therapeutically effective from about 0.1 to about 10 percent by weight, based on the composition weight, with from about 0.5 to about 5 percent by weight being preferred, and from about 2 to about 5 percent by weight being most preferred.

The isolation of the subject hydrocarbon fraction from candelilla wax is illustrated in the following example using column chromatography on silica gel with hexane as the elution solvent:

EXAMPLE 1

A glass column 50 cm in length and 3 cm in diameter is dry-packed with Silica Gel 60 of particle size 0.063–0.200 mm (70–230 mesh ASTM); purchased from E. Merck Chemical Co. The Silica Gel is oven-dried at 120° C. for 4 to 6 hours prior to use. 50 Grams of candelilla wax is dissolved in 500 mls of warm hexane and the mixture is passed through the column at ambient temperature. The eluent is collected in a suitable glass vessel. The column is then eluted with an additional 1000 mls of hexane. The eluents are pooled and evaporated to dryness under vacuum using a rotoevaporator, affording the hydrocarbon fraction of this invention a off-white crystals, m.p.=67° C.

In addition to hexane, which is preferred, other non-polar organic solvents may be used to extract the hydrocarbon fraction from candelilla wax such as, for example, an aliphatic alkane such as pentane, heptane and the like; an aromatic hydrocarbon such as benzene, toluene, xylene and the like; an ether such as diethyl ether, dioxane and the like; tetrahydrofuran; and the like aprotic solvents. With such aprotic solvents as eluents, it is preferred to use a polar stationary phase such as, for example, silica gel, in the chromatographic separation step.

Accordingly, the subject hydrocarbon fraction may be derived from candelilla wax by:

(a) dissolving candelilla wax in an organic aprotic solvent;

(b) chromatographically separating out of said candelilla wax solution the polar constituents of candelilla wax;

(c) collecting the chromatographic eluent containing the saturated hydrocarbon fraction; and (d) evaporating the organic solvent from said eluent to yield the saturated hydrocarbon fraction.

The chemical analysis of the hydrocarbon fraction obtained from Example 1 is demonstrated in the following two examples.

EXAMPLE 2

Thin Layer Chromotography (TLC): 5 microliters of chloroform containing 10 to 20 ug of the material to be tested is spotted on a 20×20 cm, 250 micron silica gel G plate. The plate is developed in toluene once, air dried and sprayed with 50% sulfuric acid. The plate is then charred on a hot plate at 220° C. All carbon containing materials appear as dark brown to black spots and the amount of carbon containing materials correlates with the intensity of the spot. Identification of compounds is accomplished by comparing the mobility of compounds to that of authentic standards. Analysis of the hydrocarbon fraction obtained from Example 1 by this TLC technique revealed the presence of saturated hydrocarbons.

EXAMPLE 3

Gas Liquid Chromatography (GLC): GLC analysis was performed on a column packed with 3% SE-30 (80/100 mesh). Temperature programming was from 120° C.–300° C. at a rate of 5° C./minute. 2 Microliters of the sample was injected and detection was accomplished by flame ionization. Identification of the chain length distribution of the candelilla wax derived hydrocarbon was accomplished by direct comparison of its chromatogram with that of a series of normal paraffins of even carbon number $C_{14}$ through $C_{34}$ and the plotting or retention times against the carbon number. Analysis of the hydrocarbon fraction obtained from Example 1 by this GLC technique shows a content of saturated straight chain hydrocarbons with chain length ranging from $C_{29}$ to $C_{33}$. The percentage of each hydrocarbon is as follows:

| | |
|---|---|
| $C_{29}$ | about 3.3% w/w |
| $C_{30}$ | about 1.1% w/w |
| $C_{31}$ | about 83.9% w/w |
| $C_{32}$ | about 1.8% w/w |
| $C_{33}$ | about 9.9% w/w |
| Total | 100.0% |

The instant invention thus provides a pharmaceutical composition for alleviating inflammation associated with skin disorders comprising a therapeutically effective anti-inflammatory amount of candelilla wax or a substantially non-polar hydrocarbon fraction derived from candelilla wax and a pharmaceutical carrier suitable for topical administration, said candelilla wax fraction consisting essentially of a mixture of saturated straight chain hydrocarbons, wherein the chain length of said hydrocarbons is from $C_{29}$ to $C_{33}$ and about 80-85 percent by weight of said mixture is the $C_{31}$ hydrocarbon.

For purposes of this invention, the amount of each hydrocarbon in the aforementioned hydrocarbon mixture, depending upon the particular natural source of the candelilla wax, may range from about to about the following indicated percentages by weight:

| | |
|---|---|
| $C_{29}$ | 3-5% |
| $C_{30}$ | 1-2% |
| $C_{31}$ | 80-85% |
| $C_{32}$ | 1-3% |
| $C_{33}$ | 9-11% |

In view of the rather non-complex makeup of the subject hydrocarbon mixture, it is obvious that said mixture may be readily formulated by simple admixture of the indicated percentages of the individual hydrocarbons. Accordingly, such formulated mixtures, which are equivalent to those extracted from the naturally occurring candelilla wax, are deemed to be included within the term "derived from candelilla wax" as used herein.

It is also quite evident that the $C_{31}$ hydrocarbon itself provides, as the predominant component of the mixture, and as exemplified hereinafter, a substantial part of the vasoconstrictive activity attributable to the subject hydrocarbon mixture, and, as such, can be used alone, thereby providing another aspect of this invention. The $C_{31}$ hydrocarbon itself may be utilized in the same manner and in the same amounts as herein described for candelilla wax itself or the hydrocarbon fraction derived therefrom, although from about 1 to about 10 percent by weight of the $C_{31}$ hydrocarbon is preferred when used by itself in the method and composition of this invention.

A particularly suitable pharmaceutical carrier in ointment form for purposes of this invention is Hydrophilic Ointment U.S.P., an oil-in-water emulsion ointment base having the formulation:

| | |
|---|---|
| Methylparaben | 0.25 g |
| Propylparaben | 0.15 g |

-continued

| | |
|---|---|
| Sodium lauryl sulfate | 10 g |
| Propylene glycol | 120 g |
| Stearyl alcohol | 250 g |
| White petrolatum | 250 g |
| Purified water | 370 g |
| To make about | 1000 g |

The stearyl alcohol and the white petrolatum are melted on a steam bath and warmed to about 75° C. The other ingredients are dissolved in the purified water and also heated to 75° C. The petrolatum phase is then added to the water phase with mixing until the mixture congeals. The resultant ointment is cooled to room temperature.

The vasoconstriction activity of candelilla wax, the subject hydrocarbon fraction and the $C_{31}$ hydrocarbon itself is demonstrated in the following invivo vasoconstrictor assay, which is a modification of the McKenzie-Stoughton Vasoconstrictor Assay described in "Method for Comparing Percutaneous Absorption of Steroids", Arch. Derm. 86:608-610, 1962.

The test was performed on a defined area of the volar aspect of the forearm in 5 subjects. The test formulations are applied under semi-occlusion to maximize differences in activity. Thus, test formulations are saturated on the absorbent cushion pad of ¾ inch bandages (Curity Curad Sheer Bandages) and the bandages taped to the forearm with no more than 7 bandages per forearm. The bandages are left on the forearm for 24 hours and then removed. The treatment sites are washed with soap and water to remove any excess material still on the skin surface. After 1 hour, the resulting blanching or whitening of the skin is then scored by two judges using the following scoring system:

0 = No blanching
1 = Barely perceptible blanching
2 = Distinct blanching with well defined outline
3 = Strong blanching An increase in blanching reflects a corresponding increase in vasoconstriction activity.

EXAMPLE 4

The experimental results on the activity of candelilla wax, the subject hydrocarbon fraction and the $C_{31}$ hydrocarbon itself in the foregoing vasoconstruction assay are set forth below. For comparative purposes, a potent commercially available steroid anti-inflammatory product, LIDEX Cream (Syntex Laboratories, Inc.), containing 0.05% of the active anti-inflammatory compound, fluocinonide, was used as a positive control. The results tabulated below are averages of at least five subjects. Products B through E were tested at the indicated % w/w concentration in the previously described Hydrophilic Ointment U.S.P.

| | Product | Blanching |
|---|---|---|
| A. | LIDEX Cream 0.05% | 3.0 |
| B. | 1% Hydrocarbon fraction obtained from Example 1 | 2.5 |
| C. | 5% Candelilla wax | 3.0 |
| D. | 2% Candelilla wax | 2.8 |
| E. | 1% $C_{31}$ Hydrocarbon | 1.5 |
| F. | Hydrophilic Ointment U.S.P. | 1.0 |

As the results indicate, LIDEX Cream 0.05% induced a very high vasoconstrictive effect with a maximum score of 3.0. The hydrocarbon fraction from candelilla wax scored 2.5 in the blanching scale, slightly lower than that of LIDEX Cream 0.05%. Both candelilla wax preparations were substantially comparable to LIDEX Cream 0.05%. Although of lesser potency, the $C_{31}$ hydrocarbon itself had a demonstrable score of 1.5 even at the low 1% concentration. The hydrophilic ointment vehicle induced a slight blanching effect with a score of 1.0.

In view of their marked vasoconstrictor activity, both candelilla wax and the subject hydrocarbon fraction are each deemed to be of value as a therapeutic agent for treatment of inflammatory skin disorders. When the compositions of the present invention are used in the treatment of such disorders, the amount of composition typically applied and treatment regimen will vary, depending upon, for example, the particular disorder being treated and its severity, the frequency of application and the area of the body which is afflicted.

For example, when the compositions of this invention are used in the topical treatment of acne, the preferred treatment will comprise applying a therapeutically effective amount of the composition to the afflicted situs on the skin. Generally, a therapeutically effective amount would be from about 1 mg/cm$^2$ to about 10 mg/cm$^2$, and preferably about 2-5 mg/cm$^2$, of the composition per day. It is preferred to cleanse the skin prior to treatment. The treatment is more effective if topical applications are made 2 to 4 times daily.

We claim:

1. A method of alleviating inflammation associated with skin disorders which comprises administering topically to the afflicted situs a therapeutically effective amount of a saturated straight chain $C_{29-33}$ hydrocarbon fraction derived from candelilla wax, wherein about 80-85 percent by weight of said fraction is the $C_{31}$ hydrocarbon, in a pharmaceutical carrier suitable for topical administration.

2. The method of claim 1 wherein said skin disorder is acne.

3. The method of claim 1 wherein the amount of said hydrocarbon fraction is from about 0.1 to about 10 weight percent.

4. The method of claim 1 wherein said hydrocarbon fraction consists essentially of a mixture of about 3.3 percent by weight $C_{29}$, about 1.1 percent by weight $C_{30}$, about 83.9 percent by weight $C_{31}$, about 1.8 percent by weight $C_{32}$ and about 9.9 percent by weight $C_{33}$ hydrocarbons.

5. A method of alleviating inflammation associated with acne which comprises administering topically to the afflicted situs from about 0.5 to about 5 percent by weight of a saturated straight chain $C_{29}$-$C_{33}$ hydrocarbon fraction derived from candelilla wax of about 3-5 percent by weight $C_{29}$, about 1-2 percent by weight $C_{30}$, about 80-85% percent by weight $C_{31}$, about 1-3 percent by weight $C_{32}$ and about 9-11 percent by weight $C_{33}$ hydrocarbons in a pharmaceutical carrier suitable for topical administration.

6. The method of claim 5 wherein the percentage of said hydrocarbon fraction is from about 2 to about 5 percent.

7. A method of alleviating inflammation associated with skin disorders which comprises administering topically to the afflicted situs a therapeutically effective amount of saturated straight chain $C_{31}$ hydrocarbon in a pharmaceutical carrier suitable for topical administration.

8. The method of claim 7 wherein the amount of said $C_{31}$ hydrocarbon is from about 1 to about 10 weight percent.

9. A method of alleviating inflammation associated with skin disorders which comprises administering topically to the afflicted situs a pharmaceutical composition consisting of a therapeutically effective amount of candelilla wax in a pharmaceutical carrier suitable for topical administration.

10. A method of alleviating inflammation associated with skin disorders which comprises administering topically to the afflicted situs a pharmaceutical composition consisting of from about 0.1 to about 10 percent by weight, based on the weight of the composition, of candelilla wax in a pharmaceutical carrier suitable for topical administration.

11. A pharmaceutical composition for alleviating inflammation associated with skin disorders comprising a therapeutically effective amount of a saturated straight chain $C_{29}$-$C_{33}$ hydrocarbon fraction derived from candelilla wax, wherein about 80-85 percent by weight of said fraction is the $C_{31}$ hydrocarbon, in a pharmaceutical carrier suitable for topical administration.

12. A pharmaceutical composition for alleviating inflammation associated with skin disorders comprising from about 0.1 to 10 percent by weight, based on the weight of the composition, of a saturated straight chain $C_{29-33}$ hydrocarbon fraction derived from candelilla wax of about 3-5 percent by weight $C_{29}$, about 1-2 percent by weight $C_{30}$, about 80-85 percent by weight $C_{31}$, about 1-3 percent by weight $C_{32}$ and about 9-11 percent by weight $C_{33}$ hydrocarbons in a pharmaceutical carrier suitable for topical administration.

13. The composition of claim 12 wherein the percentage of said hydrocarbon fraction is from about 0.5 to about 5 percent.

14. The composition of claim 12 wherein the percentage of said hydrocarbon fraction is from about 2 to about 5 percent.

15. The pharmaceutical composition of claim 12 wherein said pharmaceutical carrier is an ointment or an emulsion.

16. A pharmaceutical composition for alleviating inflammation associated with skin disorders comprising a therapeutically effective amount of saturated straight chain $C_{31}$ hydrocarbon in a pharmaceutical carrier suitable for topical administration.

17. The composition of claim 16 wherein the amount of said $C_{31}$ hydrocarbon is from about 1 to about 10 weight percent.

18. The pharmaceutical composition of claim 17 wherein said pharmaceutical carrier is an ointment or an emulsion.

* * * * *